United States Patent [19]

Seckinger

[11] 4,334,739
[45] Jun. 15, 1982

[54] METHOD OF GRAPHICALLY DISPLAYING THE RESULTS OF REPEATED PERIMETRIC EXAMINATION OF VISUAL FIELDS

[75] Inventor: Erich Seckinger, Dübendorf, Switzerland

[73] Assignee: Interzeag AG, Schlieren, Switzerland

[21] Appl. No.: 933,852

[22] Filed: Aug. 15, 1978

[30] Foreign Application Priority Data

Sep. 9, 1977 [CH] Switzerland ............... 11059/77

[51] Int. Cl.³ ................. A61B 3/00; A61B 3/02
[52] U.S. Cl. ............................ 351/39; 351/23
[58] Field of Search ............ 351/23, 24, 35, 36, 351/39

[56] References Cited

U.S. PATENT DOCUMENTS 3,664,732  5/1972  Lynn ........................ 351/24 X
3,718,386  2/1973  Lynn et al. ................ 351/23 X
4,145,123  3/1979  Krahn ........................ 351/23

OTHER PUBLICATIONS

Bedwell, American Journal of Opotometry and Archives of American Academy of Optometry, 10/67.

Primary Examiner—John K. Corbin
Assistant Examiner—Rodney Bovernick
Attorney, Agent, or Firm—Kontler, Grimes & Battersby

[57] ABSTRACT

Threshold values which are ascertained during successive static perimetric examinations of the visual field of a subject by presenting variable-intensity stimuli to selected points of a test field are permanently recorded in the form of a single graphic display. The printer which makes the permanent record is connected with a computer which controls the sequence of presentation of stimuli during each examination. If the points of presentation of stimuli overlap, the computer ascertains the arithmetic mean of corresponding threshold values which are ascertained during successive examinations or subtracts one threshold value from the other (corresponding) threshold value. Such modified threshold values are also displayed on the record, together with threshold values which are interpolated by the computer between those threshold values which are ascertained during perimetric examination.

9 Claims, 11 Drawing Figures

○ 1. TEST  ✗ INTERPOLATED THRESHOLDS
△ 2. TEST

○ 1. TEST  ✗ INTERPOLATED THRESHOLDS
△ 2. TEST
□ 3. TEST
● MEAN THRESHOLDS

METHOD OF GRAPHICALLY DISPLAYING THE RESULTS OF REPEATED PERIMETRIC EXAMINATION OF VISUAL FIELDS

BACKGROUND OF THE INVENTION

The present invention relates to perimetric examinations of visual fields. More particularly, the invention relates to a method of displaying the results of perimetric examinations. Still more particularly, the invention relates to a method of graphically displaying data which are obtained from repetitive perimetric examination of the visual field of one and the same subject.

Recent developments in perimetry, especially the computerization of perimeters, render it possible to complete perimetric examination of visual fields within a short interval of time and with a high degree of accuracy. A modern perimeter, e.g., a perimeter known as "OCTOPUS" (trademark) distributed by HITRON Corporation, Norwood, N.J. and INTERZEAG AG, Schlieren, Switzerland, is equipped with a cupola providing an illuminated screen for presentation of stimuli to a subject who is seated in front of the cupola, a computer which selects the sequence and intensity of stimuli as well as the examination program and receives and processes subject responses, an external memory for storage of the results of examinations, a typewriter keyboard connected with the computer, a printer which furnishes a graphical display of a perimetric examination, and certain optional equipment such as a rotary monitor for automatic determination of the direction of gaze. Each program involves the presentation of a group of variable-intensity stimuli at selected points of a lattice-like raster which overlies the visual field. The stimuli (short-lasting spots of light) of each group are presented at random and the intensity of each stimulus is varied until the subject response indicates the presentation of a threshold value, namely, a value which is discernible by the subject's eye with a 50-percent probability. An automatic perimeter stores a substantial number of examination programs including a program for general survey of the entire visual field and programs for the examination of selected areas or portions of such field. The printer furnishes a graphic display of the examination results, i.e., it normally imprints a sheet wherein the threshold values of a selected group of stimuli are represented by numerals, lines of different length or dots of different diameters. A presently preferred method is display by proportional areas (grey tones). The relationship of symbols or individual data on the sheet corresponds to the pattern of stimuli which were presented to the subject in the course of a perimetric examination. The display shows the distribution of threshold values over the entire visual field or over the selected area of the field. Furthermore, the display can show the distribution of threshold values over the selected area of the visual field or in a section along a straight line.

A drawback common to all presently known methods is that it is difficult to piece together the results of several successive examinations, i.e., the ophthalmologist does not obtain a graphic display which constitutes a composite representation of data obtained as a result of two or more discrete examinations of one and the same area or of different areas of the visual field of a subject. In other words, the printer merely furnishes data denoting the results of discrete examinations. The problem is especially pronounced when some or all of successive examinations do not involve the determination of threshold values in different areas of the visual field.

OBJECTS AND SUMMARY OF THE INVENTION

An object of the invention is to provide a novel and improved method of displaying the results of perimetric examinations of visual fields.

Another object of the invention is to provide a novel and improved method of graphically displaying the results of repeated perimetric examination of the visual field of one and the same subject.

A further object of the invention is to provide a method which furnishes a readily interpretable graphic display of the results of two or more successive perimetric examinations of a visual field, either of one and the same area of the visual field (e.g., the entire field) or of two or more different or partly overlapping areas of the visual field.

An additional object of the invention is to provide a method which can be resorted to for obtaining a simple display of data obtained as a result of any practical number of consecutive perimetric examinations of the visual field of a subject.

An ancillary object of the invention is to provide a method which can be practiced by resorting to available perimeters.

Another object of the invention is to provide a method of displaying the results of successive perimetric examinations in such a way that the progress of a disease or the progress of a healing process can be readily followed by a physician or even by a skilled technician.

The invention resides in the provision of a method of making records of the results of repeated perimetric examination of the visual field of a subject. The method comprises the steps of presenting to the subject at timely spaced intervals groups of variable-intensity stimuli in the form of light spots at selected points of a test field which is oriented with respect to the direction of gaze of the subject, storing during each presentation the perceived threshold values of the stimuli of the respective group, and forming a single display, preferably a graphic display, with data denoting the stored threshold values.

If the examination program (i.e., the program of presentation of a group of stimuli) which has been selected for a preceding examination is not identical with the program which is presented during the next-following examination, the group of stimuli which are presented in the course of the preceding examination normally includes at least some stimuli without corresponding stimuli in the group which is presented in the course of the next-following examination or vice versa. In such instances, the display forming step includes displaying data denoting the threshold values of stimuli presented solely during the preceding examination and threshold values of stimuli which are presented solely in the course of the next-following examination.

The method can further comprise the step of interpolating threshold values between the threshold values of stimuli of one or more groups which are presented in the course of the respective examination(s). The display forming step then includes displaying the interpolated threshold values.

If the points of presentation of at least some stimuli of a first group which is presented during a preceding examination coincide with the points of presentation of at least some stimuli of a second group which is presented during a next-following examination, the method preferably further comprises the step of modifying the threshold value of each stimulus of the first group as a function of the threshold value of the corresponding stimulus of the second group. The display forming step then includes forming the single display with data denoting the modified threshold values, i.e., such display will then contain data denoting the unmodified threshold values (if any) of the first group of stimuli, data denoting the unmodified threshold values (if any) of the second group of stimuli, and data denoting the modified threshold values.

The modifying step may include establishing (e.g., by resorting to a computer) an arithmetic mean between the threshold values of corresponding stimuli of the first and second groups. Alternatively, the modifying step may include subtracting the threshold value of one of the first and second groups of stimuli from the corresponding threshold value of the other of the first and second groups of stimuli.

The threshold values of each group of stimuli are preferably retained in storage (e.g., in an external memory which is connected with the computer) after completion of the display forming step.

The perimetric examination is preferably a static examination.

The novel features which are considered as characteristic of the invention are set forth in particular in the appended claims. The improved method itself, however, together with additional features and advantages thereof, will be best understood upon perusal of the following detailed description of certain specific embodiments of an automatic perimeter with reference to the accompanying drawing.

DESCRIPTION OF THE PREFERRED EMBODIMENTS

Figure 1:
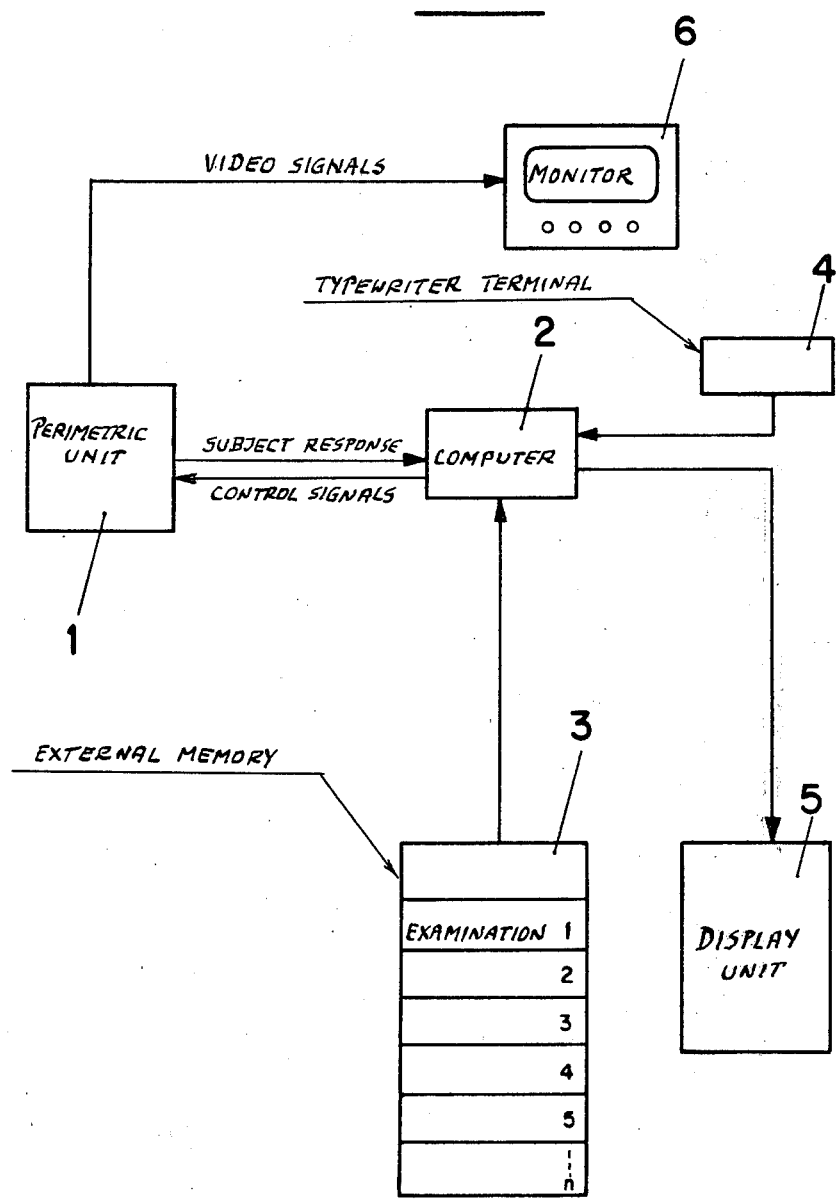
FIG. 1 is a block diagram showing certain component parts of a computerized perimeter machine which can be utilized for the practice of my method.
Figure 2:
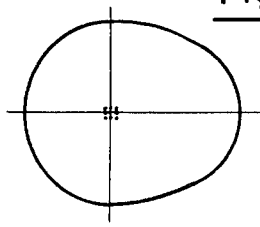
FIG. 2 is a two-dimensional illustration of the visual field of a subject's eye, further showing the examination program for static perimetry of the center of the visual field.

FIG. 1 shows certain component parts of an automatic perimeter which comprises a perimetric unit 1 with a customary cupola having a screen for presentation of variable-intensity stimuli (light spots) to the eye of a subject who is seated in front of the cupola. The unit 1 further comprises a customary projector for stimuli and is connected with a computer 2 having a built-in memory (not specifically shown). The computer 2 receives patient responses from the unit 1 and transmits control signals for presentation of stimuli in accordance with a selected program. The computer 2 is further connected with an external memory 3 (e.g., a floppy disc), with a typewriter terminal 4 and a display unit here shown as a printer 5 which furnishes data denoting the results of perimetric examinations. Still further, the perimeter comprises a monitor 6 which receives video signals from the perimetric unit 1 and serves to automatically check the fixation of a subject's gaze. The computer 2 may be an Intel MDS 800 micro-processor with random access memory of 32000 8-bit words.

Figure 3:
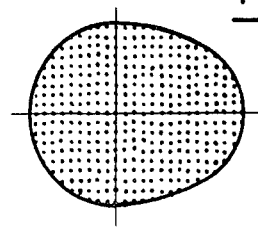
FIG. 3 illustrates the examination program for static screening perimetry including a general survey of the entire visual field.

The memory 3 includes means for storing information pertaining to successive perimetric examinations. For example, the first examination may cover the entire visual field of a subject (this is shown in FIG. 3) and the next examination or examinations may cover certain portions of the visual field (as shown in FIGS. 2 and 4 to 7). The results of all examinations (i.e., two or more successive examinations) are obtained in a manner as illustrated in the flow chart of FIG. 8. The terminal 4 serves to furnish the computer 2 with information pertaining to the number and sequence of programs which are required by a physician. The computer 2 then addresses the memory 3 to receive the desired programs each consisting of a group of stimuli of variable intensity. Each group is presented to the subject on the screen of the cupola in the unit 1, and the subject sends responses (e.g., by actuating a suitable response device) until the computer 2 accumulates data denoting the threshold values of all stimuli, i.e., such stimulus values which are perceived by the subject with a 50-percent probability. Upon completion of two or more successive examinations, the computer 2 receives a signal to process the information, preferably by calculating an arithmetic mean of each pair of corresponding threshold values which are obtained for the same point of the raster during successive examinations. The manner in which each examination proceeds is fully described in the commonly owned copending application Ser. No. 933,851 filed Aug. 15, 1978 for "Method of perimetric examination of visual fields". The disclosure of said copending application by the same inventor is incorporated herein by reference.

The computer 2 further proceeds to interpolate threshold values between the threshold values which were obtained as a result of actual presentation of stimuli to the subject. Finally, the computer 2 transmits a signal to the printer 5 which furnishes a single graphic record of the results of two or more successive examinations. The record can display the information in the form of proportional areas (grey tones). This is a two-dimensional graphical display whereby the third component (sensitivity) is presented by dots whose areas are inversely proportional to the sensitivity. Such types of display are preferred at this time because they can be produced in a simple printer and can be readily interpreted. A legend can be provided on the sheet in order to enable the physician to read off the quantitative value at any point of the graph.

Figure 9:
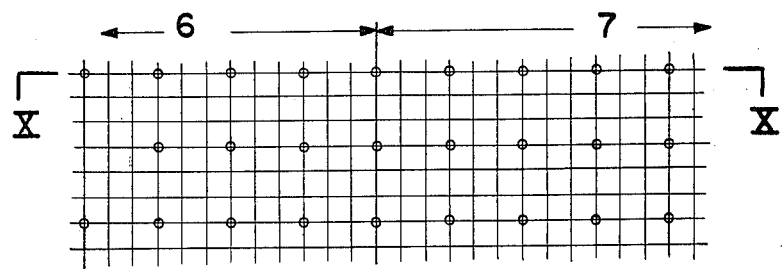
FIG. 9 shows a portion of a lattice-like raster which is placed over the visual field.
Figure 10:
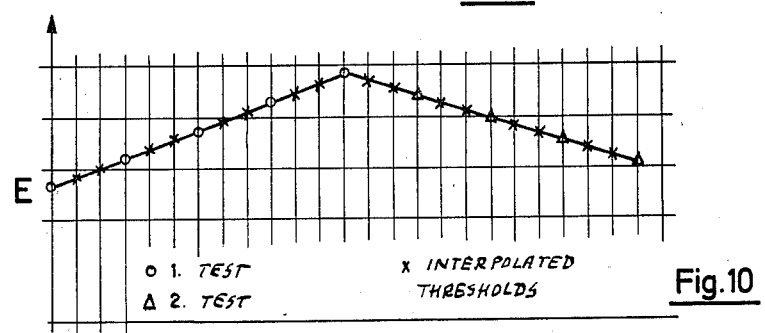
FIG. 10 is a quantitative representation of the results of two successive examinations, showing the threshold values along the line X—X of FIG. 9

The manner of carrying out two successive examinations of the visual field of a subject is illustrated in FIGS. 9 and 10. FIG. 9 shows a raster which is placed over the screen in the cupola of the perimetric unit 1 and each point of which represents the potential location of presentation of a stimulus. The area 6 of the raster is used for presentation of stimuli in the course of a first examination, and the next examination covers the area 7. The circles denote the points of presentation of stimuli; it will be noted that a stimulus is presented to the subject at each third point of the raster. The groups of stimuli for presentation to the subject during two discrete examinations covering the areas 6 and 7 are furnished by the external memory 3.

The threshold values which are ascertained during two consecutive examinations (areas 6 and 7 of the raster of FIG. 9) are shown in FIG. 10. The threshold values represent those intensities of stimuli which are determined along the line X—X of FIG. 9. The intensities E of stimuli are measured along the ordinate. By way of example, the area 6 of FIG. 9 may correspond to the dotted area of the visual field in FIG. 4, and the area 7 may correspond to the dotted area of the visual field in FIG. 5. The threshold values wich are respectively ascertained during examination of areas 6 and 7 are stored in separate compartments of the memory 3. If the computer 2 thereupon receives from the keyboard of the typewriter terminal 4 a signal to initiate the formation of a single display, the computer pieces together a composite group of data denoting the threshold values of two examinations and the corresponding graphical display is furnished by the printer 5. Thus, and referring to the curve of FIG. 10, the display shows the threshold values along the line X—X of the raster of FIG. 9 in a manner to denote their quantitative values. Accordingly, the display is a composite graphical representation of the results of two discrete perimetric examinations of two different portions or areas of the visual field. In other words, there is no overlap between the threshold values which were obtained on examination of the areas 6 and 7 because such areas represent two different portions of the visual field of one and the same subject.

In an analogous manner, the display can constitute a graph of threshold values which are obtained upon examination of the dotted areas shown in FIGS. 2 and 4, 2 and 5, 2 and 6, 2 and 7, 4 and 6, 4 and 7, 5 and 6, 6 and 7, 2 and 4 and 5, 2 and 4 and 6, 2 and 4 and 7, 2 and 4 and 5 and 6 (almost equal to 3), 4 and 5 and 6, and/or any other combination which does not entail ascertainment of overlapping threshold values during two or more consecutive examinations.

The computer 2 interpolates threshold values for all those points of the raster which are not covered by the selected programs. In FIG. 10, such interpolated threshold values are denoted by the symbols "x". Interpolation is necessary or desirable because, with the exception of the program of FIG. 7, all other programs normally involve the presentation of stimuli at some but not all points of the corresponding portion of the raster. In FIG. 10, a threshold value is ascertained by actual testing at each third point of the raster. This shortens the test and, in combination with interpolation, insures a sufficiently accurate examination of the selected portions of the visual field. The threshold values which are ascertained during examination of the visual field portion corresponding to the part 6 of the raster are denoted by circles, and the threshold values which are ascertained during examination of that field portion which corresponds to the part 7 of the raster are denoted by triangles. The interpolated threshold values ("x") lie on lines connecting the neighboring threshold values ascertained by actual presentation of stimuli to the corresponding portions of the visual field.

Figure 7:
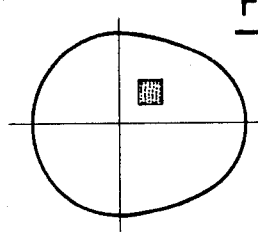
FIG. 7 shows the examination program for static precision perimetry of a selected portion of the visual field.
Figure 8:
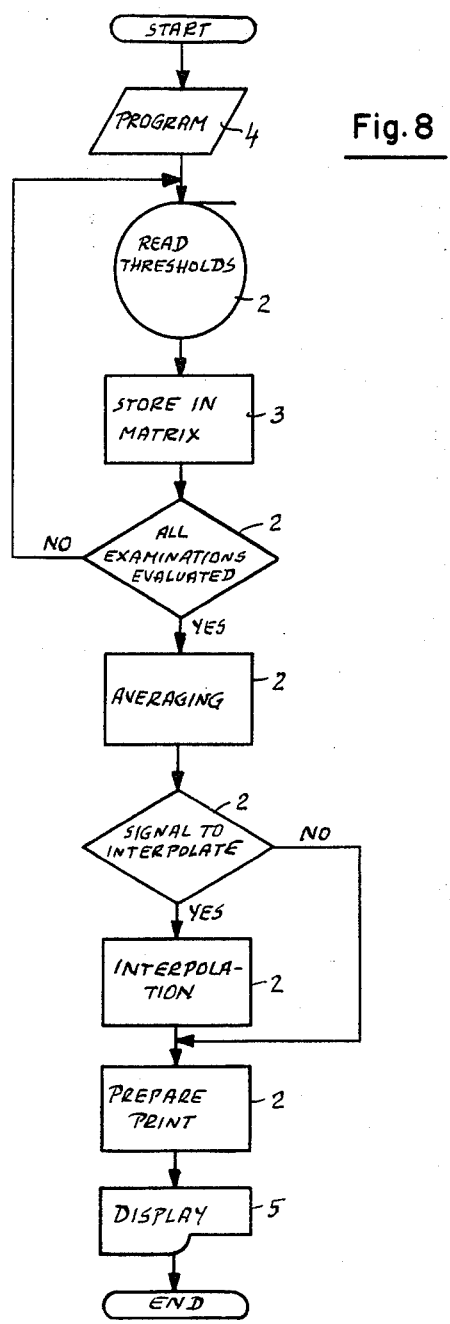
FIG. 8 is a flow chart representing the mode of operation of the perimeter machine of FIG. 1.
Figure 11:
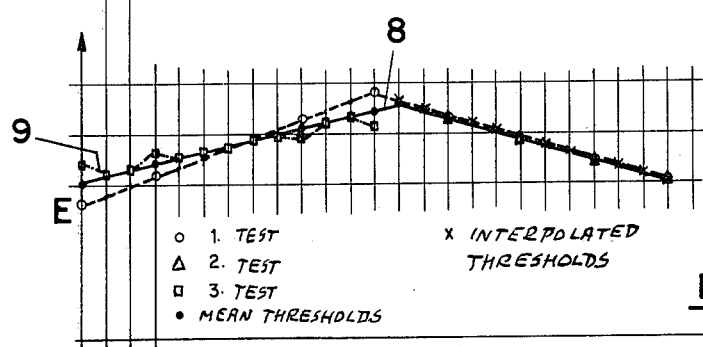
FIG. 11 is a similar quantitative representation of the results of a series of additional examinations.

If the examinations Nos. 1 and 2 (parts 6 and 7 of the raster of FIG. 9) are followed by a third examination which involves renewed presentation of stimuli to the part 6 of the raster (or the presentation of stimuli in accordance with the program of FIG. 7), and the threshold values which are ascertained during such third examination correspond to those shown in the form of squares on the phantom line 9 of FIG. 11, the computer 2 modifies each threshold value (circle) of the first examination as a function of the corresponding threshold value (square) of the third examination, for example, by calculating the arithmetic mean of circular and corresponding square threshold values. Such modified threshold values lie on the curve 8 of FIG. 11 and are denoted by black dots.

Actually, the curve 9 of FIG. 11 represents the threshold values which are ascertained in accordance with the program of FIG. 7 (note that each and every print of the raster has been presented a stimulus). The computer calculates modified threshold values (dots in FIG. 11) where the next-following examination involves the determination of threshold values (squares) at raster points at which the threshold values (circles) were ascertained during a preceding examination. The threshold values (triangles on the line 8) for which no counterparts were ascertained during a next-following examination remain unchanged. The result of the third examination is stored in a separate compartment of the memory 3 and the printer 4 furnishes a graph wherein the threshold values along the line X—X of FIG. 9 correspond to those (dots and triangles) on the line 8 of FIG. 11.

Figure 4:
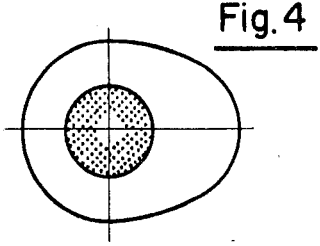
FIG. 4 shows the examination program for static perimetry of the inner area of the visual field between 0°–30°.
Figure 5:
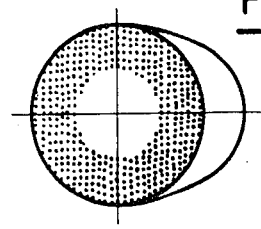
FIG. 5 shows the examination program which is complementary to the program of FIG. 4 and includes static perimetry in the intermediate range of the visual field between 30°–60°.
Figure 6:
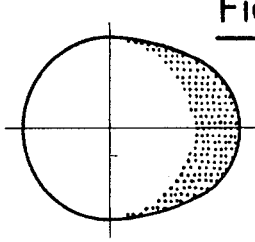
FIG. 6 shows the examination program for static perimetry of the outer range of the visual field between 60°–90°.

If the examination No. 4 involves renewed presentation of the program of FIG. 4 (area 6 of the raster) or FIG. 7, the freshly ascertained threshold values are used to modify the corresponding threshold values on the curve 8.

Interpolation of threshold values between neighboring threshold values which are ascertained during a perimetric examination is desirable but optional. Thus, and referring to the curve of FIG. 10, the right-hand part of this curve could consist of discrete triangles and/or the left-hand part of the curve could consist of discrete circles.

It is also within the purview of the invention to program the computer 2 in such a way that it modifies a previously ascertained threshold value by a freshly ascertained threshold value at the same point of the raster by subtracting the quantitative value of one threshold value from the quantitative value of the other threshold value. Analogously, the computer can be designed to subtract the modified threshold values which are obtained from a first series of successive examinations from the modified (or unmodified) threshold values which are obtained from another series of examinations (or a single next-following examination).

In order to reduce the duration of the first examination, the subject is preferably presented a group of stimuli corresponding to the mean threshold values for the age group of the subject.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

I claim:

1. A method of making records of the results of perimetric examinations of the visual field of a subject, comprising the steps of presenting to the subject during each of at least two separate examinations a group of variable intensity stimuli at selected points of a test field which covers an area of the visual field that is individually selected for each of said examinations as to its outline and orientation with respect to the direction of gaze of the subject; storing, during each examination, the perceived threshold values of the stimuli of the respective group; and forming a single composite graphical display with data denoting said stored threshold values obtained during said separate examinations.

2. A method as defined in claim 1, further comprising the step of interpolating additional threshold values between the threshold values of at least one of said groups of stimuli, said display forming step including forming said single display with data denoting said interpolated threshold values.

3. A method as defined in claim 1, wherein the points of presentation of at least some stimuli of a first group which is presented during a preceding examination coincide with the points of presentation of at least some stimuli of a second group which is presented during a next-following examination, and further comprising the step of modifying the threshold value of each such stimulus of said first group whose point of presentation coincides with the point of presentation of a stimulus of the second group as a function of the threshold value of the corresponding stimulus of said second group, said display forming step including forming said single display with data denoting said modified threshold values.

4. A method as defined in claim 3, wherein said modifying step comprises establishing an arithmetic mean between the threshold values of corresponding stimuli of said first and second groups.

5. A method as defined in claim 3, wherein said modifying step comprises subtracting the threshold value of one of said first and second groups from the corresponding threshold value of the other of said first and second groups.

6. A method as defined in claim 3, wherein the number of stimuli in one of said first and second groups is different from the number of stimuli in the other of said first and second groups.

7. A method as defined in claim 1, further comprising the step of retaining the threshold values of each of said groups of stimuli in storage after completion of said display forming step.

8. A method as defined in claim 1, wherein the points of presentation of one of said groups of stimuli do not coincide with the points of presentation of another of said groups of stimuli.

9. A method as defined in claim 1, wherein each perimetric examination is a static examination.

* * * * *